US011806330B2

(12) United States Patent
Morch et al.

(10) Patent No.: US 11,806,330 B2
(45) Date of Patent: *Nov. 7, 2023

(54) PACA AND CABAZITAXEL FOR ANTI-CANCER TREATMENT

(71) Applicants: SINTEF TTO AS, Trondheim (NO); Oslo Universitetssykehus HF, Oslo (NO)

(72) Inventors: Yrr Morch, Trondheim (NO); Einar Sulheim, Trondheim (NO); Kjersti Flatmark, Blommenholm (NO); Karianne Giller Fleten, Oslo (NO); Per Stenstad, Trondheim (NO); Heidi Johnsen, Trondheim (NO); Ruth Schmid, Tiller (NO)

(73) Assignees: SINTEF TTO AS, Trondheim (NO); OSLO UNIVERSITETSSYKEHUS HF, Oslo (NO)

(*) Notice: Subject to any disclaimer, the term of this patent is extended or adjusted under 35 U.S.C. 154(b) by 0 days.

This patent is subject to a terminal disclaimer.

(21) Appl. No.: 16/366,596

(22) Filed: Mar. 27, 2019

(65) Prior Publication Data
US 2019/0298682 A1 Oct. 3, 2019

(30) Foreign Application Priority Data

Mar. 27, 2018 (NO) .................................. 20180429

(51) Int. Cl.
| A61K 31/337 | (2006.01) |
| A61K 9/51 | (2006.01) |
| A61K 9/00 | (2006.01) |
| A61P 35/04 | (2006.01) |
| A61K 47/60 | (2017.01) |
| A61K 9/107 | (2006.01) |
| A61K 9/16 | (2006.01) |
| B82Y 5/00 | (2011.01) |

(52) U.S. Cl.
CPC .......... *A61K 31/337* (2013.01); *A61K 9/0019* (2013.01); *A61K 9/1075* (2013.01); *A61K 9/1641* (2013.01); *A61K 9/5138* (2013.01); *A61K 9/5146* (2013.01); *A61K 9/5192* (2013.01); *A61K 47/60* (2017.08); *A61P 35/04* (2018.01); *B82Y 5/00* (2013.01)

(58) Field of Classification Search
None
See application file for complete search history.

(56) References Cited

U.S. PATENT DOCUMENTS

| 2008/0182776 | A1* | 7/2008 | Lee ....................... A61K 9/5192 424/489 |
| 2010/0015165 | A1 | 1/2010 | Landfester et al. |
| 2010/0209354 | A1 | 8/2010 | Horcajada-Cortes et al. |
| 2016/0129132 | A1 | 5/2016 | Schmid et al. |
| 2018/0185321 | A1* | 7/2018 | Taub ..................... A61K 31/337 |
| 2019/0216839 | A1* | 7/2019 | Miyano ............... A61K 31/7088 |
| 2020/0023073 | A1 | 1/2020 | Morch et al. |
| 2020/0061019 | A1 | 2/2020 | Morch et al. |
| 2021/0113482 | A1 | 4/2021 | Morch et al. |
| 2022/0257525 | A1 | 8/2022 | Morch et al. |

FOREIGN PATENT DOCUMENTS

| CN | 107115532 A | 9/2017 |
| EP | 2508207 A1 | 10/2012 |
| EP | 2913065 A1 | 9/2015 |
| NO | 342271 B1 | 4/2018 |
| WO | 2006016020 A2 | 2/2006 |
| WO | 2006127953 A2 | 11/2006 |
| WO | 2008003706 A1 | 1/2008 |
| WO | WO 2014191502 * | 4/2014 |
| WO | 2014191502 A1 | 12/2014 |
| WO | 2016083533 A1 | 6/2016 |
| WO | 2016134115 A1 | 8/2016 |
| WO | 2017143967 A1 | 8/2017 |
| WO | 2017204475 A1 | 11/2017 |
| WO | 2018060437 A1 | 4/2018 |

OTHER PUBLICATIONS

Hallaj-Nezhadi et al. "Intraperitoneal delivery of nanoparticles for cancer gene therapy" 2013.*
Tsao et al. "The role of cabazitaxel in the treatment of metastatic castration-resistant prostate cancer" 2014.*
Petrillo et al. "Cytoreductive Surgery Plus Platinum-Based Hyperthermic Intraperitonal Chemotherapy in Epithelial Ovarian Cancer: A Promising Integrated Approach to Improve Locoregional control". 2016.*
Burns Polycyanoacrylates 2016.*
Crespy et al. "Miniemulsion polyemerization as a versatile tool for the synthesis of functionalized polymers".*
Dakwar et al. Nanomedicine-based intraperitoneal therapy for the treatment of peritoneal carcinomatosis—Mission possible? Advanced Drug Delivery Reviews vol. 108, Jan. 1, 2017, pp. 13-24.*
Sulheim "Cytotoxicity of Poly(alkylcyanoacrylate) Nanoparticles" Nov. 2017.*
Yordanov "Poly(alkyl cyanoacrylate) nanoparticles as drug carriers 33 years later" 2013.*
Flatmark et al., "Exploring the peritoneal surface malignancy phenotype—a pilot immunohistochemical study of human pseudomyxoma peritonei and derived animal models," Human Pathology, 2010, vol. 41(8), pp. 1109-1119.
Flatmark et al., "Immunotoxin targeting EpCAM effectively inhibits peritoneal tumor growth in experimental models of mucinous peritoneal surface malignancies," International Journal of Cancer, 2013, vol. 133(6) pp. 1497-1506.
Flatmark et al., "Pseudomyxoma peritonei—two novel orthotopic mouse models portray the PMCA-I histopathologic subtype," BMC Cancer, 2007, vol. 7:116, pp. 1-7.

(Continued)

Primary Examiner — Danah Al-Awadi
(74) Attorney, Agent, or Firm — Karen A. LeCuyer; DeWitt LLP

(57) ABSTRACT

Described herein is an active ingredient encapsulated into poly (alkyl cyanoacrylate) nanoparticles and their use in anti-cancer treatments by intraperitoneal administration.

7 Claims, 1 Drawing Sheet

(56) References Cited

OTHER PUBLICATIONS

International Preliminary Report on Patentability; International Application No. PCT/EP2017/074798; International Filing Date Sep. 29, 2017; dated Aug. 21, 2018; 17 pages.

International Search Report and Written Opinion, International Application No. PCT/EP2017/074798; International Filing Date Sep. 29, 2017, dated Jan. 12, 2017; 9 pages.

Kumari et al., "Biodegradable polymeric nanoparticles based drug delivery systems," Colloids and Surfaces B: Biointerfaces, 2010, vol. 75, pp. 1-18.

Matsumura et al., "A new concept for macromolecular therapeutics in cancer chemotherapy: mechanism of tumoritropic accumulation of proteins and the antitumor agent smancs," Cancer Research, 1986, vol. 46 (12 Pt 1), pp. 6387-6392.

Peracchia et al., "Development of sterically stabalized poly(isobutyl 2-cyanoacrylate) nanoparticles by chemical coupling of poly(ethylene glycol)," Journal of Biomedical Materials Research, 1997, vol. 34, pp. 317-326.

Prabhakar et al., "Challenges and key considerations of the enhanced permeability and retention effect for nanomedicine drug delivery in oncology," Cancer Research, 2013, vol. 73 (8), pp. 2412-2417.

Shi et al., "Cancer nanomedicine: progress, challenges and opportunities," Nat Rev Cancer, 2017, vol. 17 (1), pp. 20-37.

Snipstad et al., "Ultrasound Improves the Delivery and Therapeutic Effect of Nanoparticle-Stabilized Microbubbles in Breast Cancer Xenografts," Ultrasound Med Biol., 2017, vol. 43 (11), 2651-2669.

Sulheim et al., "Cellular uptake and intracellular degradation of poly(alkyl cyanoacrylate) nanoparticles," Journal of Nanobiotechnology, 2016, vol. 14 (1), pp. 1-14.

Sulheim et al., "Cytotoxicity of Poly(Alkyl Cyanoacrylate) Nanoparticles," International Journal of Molecular Sciences, 2017, vol. 18., 2454, pp. 1-17.

Torchilin et al., "Multifunctional, stimuli-sensitive nanoparticulate systems for drug delivery," Nat. Rev. Drug Discov, 2014, vol. 13(11), pp. 813-827.

Vrignaud et al., "Preclinical antitumor activity of cabazitaxel, a semisynthetic taxane active in taxane-resistant tumors," Clinical Cancer Research, 2013, vol. 19 (11), pp. 2973-2983.

Zhang et al., "Preparation, characterization and biocompatibility of poly(ethylene glycol)-poly(n-butyl cyanoacrylate) nanocapsules with oil core via miniemulsion polymerization," European Polymer Journal, 2008, vol. 44, Issue 6, pp. 1654-1661.

Bensaid et al.; "Y-Shaped mPEG-PLA Cabazitaxel Conjugates: Well-Controlled Synthesis by Organocatalytic Approach and Self-Assembly into Interface Drug-Loaded Core-Corona Nanoparticles"; Biomacromolecules; vol. 14, 2013, pp. 1189-1198.

Daisuke et al.; "Intraperitoneal chemotherapy for gastric cancer with peritoneal metastasis"; Gastric Cancer, vol. 20, Issue No. 1; 2016; pp. 111-121.

Fusser et al.; "Cabazitaxel-loaded Poly(2-ethylbutyl cyanoacrylate) nanoparticles improve treatment efficacy in a patient derived breast cancer xenograft"; Journal of Controlled Release, vol. 293; 2018; pp. 190-192.

Kamei et al.; "Spatial distribution of intraperitoneally administrated paclitaxel nanoparticles solubilized with poly (2-methacryloxyethyl phosphorylcholine-co n-butyl methacrylate) in peritoneal metastatic modules"; Cancer Science, vol. 102, Issue No. 1; 2010; pp. 200-205.

Lu et al.; "Paclitaxel nanoparticle inhibits growth of ovarian cancer xenografts and enhances lymphatic targeting", Cancer Chemotherapy and Pharmacology, vol. 59, Issue No. 2; 2006; pp. 175-181.

Hallaj-Nezhadi et al.; "Intraperitoneal delivery of nanoparticles for cancer gene therapy"; Future Oncology, vol. 9, Issue No. 1; 2013; pp. 59-68.

Tsao et al.; "The role of cabazitaxel in the treatment of metastatic castration-resistant prostate cancer"; Therapeutic Advances in Urology, vol. 6, Issue No. 3; 2014; pp. 97-104.

Vrignaud, P. et al.; "Preclinical Antitumor Activity of Cabazitaxel, a Semisynthetic Taxane Active in Taxane-Resistant Tumors"; Clinical Cancer Research, vol. 19, Issue No. 11; 2013; pp. 2973-2983.

Yordanov, G.; "Poly(alkyl cyanoacrylate) nanoparticles as drug carriers: 33 years later"; Bulgarian Journal of Chemistry, vol. 1, Issue No. 2; 2012; pp. 61-73.

Hu, X.; "Docetaxel-Loaded Cholesterol-PEG Co-Modified Poly (n-Butyl) Cyanoacrylate Nanoparticles for Antitumor Drug Pulmonary Delivery: Preparation, Characterization, and in vivo Evaluation"; International Journal of Nanomedicine, vol. 15; 2020; pp. 5361-5376.

Huang, C.; "Synthesis of high loading and encapsulation efficient paclitaxel-loaded poly(n-butyl cyanoacrylate) nanoparticles via miniemulsion"; International Journal of Pharmaceutics, vol. 338; 2007; pp. 267-275.

Dieras, V. et al.; "Cabazitaxel in patients with advanced solid tumours: Results of a Phase I and pharmacokinetic study"; European Journal of Cancer, vol. 49; 2013; pp. 25-34; DOI: http://dx.doi.org/10.1016/j.ejca.2012.07.008.

Hekmatara, T. et al.; "Encapsulation of Water-Insoluble Drugs in Poly(butyl cyanoacrylate) Nanoparticles"; Journal of Nanoscience and Nanotechnology, vol. 9; 2009; pp. 5091-5098; DOI: 10.1166/jnn.2009.GR05.

* cited by examiner

PACA AND CABAZITAXEL FOR ANTI-CANCER TREATMENT

CROSS-REFERENCE TO RELATED APPLICATIONS

This application claims priority to NO20180429 filed on Mar. 27, 2018, which is incorporated herein by reference in its entirety.

FIELD OF DISCLOSURE

The disclosure is related to the field of nanoparticles and medical treatment. In particular, it relates to an active ingredient encapsulated into poly (alkyl cyanoacrylate) nanoparticles and their use in anti-cancer treatments by intraperitoneal administration.

BACKGROUND

The use of nanotechnology in medicine offers many exciting possibilities with potential in a number of medicinal applications envisaged. In particular, nanomedicine is expected to lead to big improvements in the treatment of complex diseases. Two areas in which the use of nanoparticles has begun to demonstrate particular value are drug delivery and molecular imaging.

Poly(alkyl cyanoacrylate) (PACA) was first developed and approved as a surgical glue. PACA nanoparticles (NPs) have later demonstrated promising abilities as a drug carrier, being biodegradable and allowing high drug loading capacity.

WO2014191502 A1 discloses a one-step polymerization process for preparing stealth NPs of PACA homopolymer or copolymer comprising anionic polymerization of an oil-in-water miniemulsion. As disclosed, by utilizing a miniemulsion in combination with a particular class of polyalkylene glycol derivatives, it is possible to covalently attach targeting moieties to polyalkylene glycols, thereby enabling the simultaneous introduction of a targeting group and formation of a stealth corona. It is described that the miniemulsion may contain active agents, and a list of therapeutic agents are disclosed. However, none of the examples include encapsulation of any of these agents, and neither in vitro nor in vivo data are disclosed.

Although new, targeted treatment options and immunotherapy are being developed, chemotherapy is still the main therapeutic option for patients with advanced cancer. However, the therapeutic effect is not sufficient for certain cancer types and the treatment also results in severe side effects. Several products of drug-loaded NPs have reached the market, and many new product candidates are in clinical trials. These aspects, including the challenges and opportunities of using nanoparticles in cancer drug delivery, have been discussed in multiple reviews and commentaries including Shi et al. (Shi, J.; Kantoff, P. W.; Wooster, R.; Farokhzad, O. C., Cancer nanomedicine: progress, challenges and opportunities. *Nat Rev Cancer* 2017, 17 (1), 20-37) and Torchilin (Torchilin, V. P., Multifunctional, stimuli-sensitive nanoparticulate systems for drug delivery. *Nat. Rev. Drug Discov* 2014, 13 (11), 813-827). In addition to improving efficacy by benefiting from the enhanced permeability and retention (EPR) effect (Matsumura, Y.; Maeda, H., A new concept for macromolecular therapeutics in cancer chemotherapy: mechanism of tumoritropic accumulation of proteins and the antitumor agent smancs. *Cancer Res* 1986, 46 (12 Pt 1), 6387-6392), NP encapsulated drug delivery may demonstrate reduced toxicity. The main advantage of the drug-loaded NPs in the market is that they give less adverse effects than free drug, while the therapeutic efficacy is rather similar, as described in Parahbakar et al. (Prabhakar, U.; Maeda, H.; Jain, R. K.; Sevick-Muraca, E. M.; Zamboni, W.; Farokhzad, O. C.; Barry, S. T.; Gabizon, A.; Grodzinski, P.; Blakey, D. C., Challenges and key considerations of the enhanced permeability and retention effect for nanomedicine drug delivery in oncology. *Cancer Res* 2013, 73 (8), 2412-7).

In Snipstad et al. (Snipstad, S.; Berg, S.; Morch, Y.; Bjorkoy, A.; Sulheim, E.; Hansen, R.; Grimstad, I.; van Wamel, A.; Maaland, A. F.; Torp, S. H.; Davies, C. L., Ultrasound Improves the Delivery and Therapeutic Effect of Nanoparticle-Stabilized Microbubbles in Breast Cancer Xenografts. *Ultrasound Med Biol* 2017, 43 (11), 2651-2669), the medical use of PEGylated PEBCA NPs in combination with microbubbles (MBs) and ultrasound is described. The drug delivery system as described consists of microbubbles stabilized by polymeric nanoparticles (NPMBs), which enables ultrasound-mediated drug delivery. The NPs are synthesized by miniemulsion polymerization. It is disclosed NPs containing cabazitaxel (CBZ), and in vitro toxicity of these NPs in triple-negative human breast adenocarcinoma cells, MDA-MB-231. The in vivo data of the drug delivery system disclosed in Snipstad et al. described the therapeutic effect achieved by NP-stabilized MBs on localized, solid tumors, and how an improved effect is achieved by applying focused ultrasound. Taxanes are important chemotherapeutic agents with proven efficacy in many human cancers. Taxanes include paclitaxel, docetaxel, cabazitaxel (CBZ) and their pharmaceutically acceptable salts. Paclitaxel was originally derived from the Pacific yew tree. Docetaxel is a semi-synthetic analogue of paclitaxel. CBZ, which has been characterized by Vrignaud et al. (Vrignaud, P.; Semiond, D.; Lejeune, P.; Bouchard, H.; Calvet, L.; Combeau, C.; Riou, J. F.; Commercon, A.; Lavelle, F.; Bissery, M. C., Preclinical antitumor activity of cabazitaxel, a semisynthetic taxane active in taxane-resistant tumors. *Clin Cancer Res* 2013, 19 (11), 2973-83), is a relatively novel semi-synthetic taxane derivative. CBZ has a potent cytostatic effect by microtubule stabilization, but its use has been limited due to its toxicity. CBZ has been included in several clinical trials investigating efficacy against several types of cancer. It has been approved by the US Food and Drug Administration (FDA) for treatment of refractory prostate cancer as a second line drug after docetaxel chemotherapy. Taxanes present difficulties in formulation as medicines because they are poorly soluble in water.

It is therefore desirable, and hence an object of the present disclosure, to develop a new drug delivery system which is capable of effectively delivering a therapeutic agent to a specific location. In particular, a drug delivery system which demonstrates efficacy in addition to fewer adverse side effects would be desirable.

It is further desired if the new drug delivery system is capable of delivering hydrophobic and/or poorly soluble therapeutic agents.

SUMMARY

In a first aspect, provided herein is a drug delivery system comprising poly (alkyl cyanoacrylate) (PACA) nanoparticles (NPs) and cabazitaxel (CBZ), or a pharmaceutically acceptable salt thereof, for treatment of cancer by administration intraperitoneally to a subject in need thereof.

In an embodiment of this aspect, the drug delivery system does not comprise NP-stabilized microbubbles (MBs). In another embodiment, the drug delivery system does not comprise NPs that stabilize the MBs or NPs that are used to stabilize gas-filled MBs. In another embodiment, the drug delivery system does not comprise NPs that are associated with the MBs. In yet another embodiment, the drug delivery system does not comprise gas-filled MBs. In a further embodiment, the drug delivery system does not comprise MBs.

In a further embodiment, the PACA NPs are produced according to a miniemulsion anionic polymerization process.

In another embodiment, the PACA NP are optionally PEGylated.

In yet another embodiment, the PACA NP encapsulate CBZ, i.e. the CBZ is loaded within the nanoparticle.

In a further embodiment, the alkyl chain of the cyanoacrylate is selected from the group consisting of n-butyl- (BCA), 2-ethyl butyl (EBCA), polyisohexyl (IHCA) and octyl cyanoacrylate (OCA).

In another embodiment, the NPs are further surface modified by a targeting moiety.

According to different embodiments of the first aspect, the PACA NP has dimensions below 800 nm, such as in a range selected from 1-800 nm or 10-500 nm or 70-150 nm.

In yet other embodiments, the CBZ comprises 1-90 wt % of the total weight of the NP, preferentially 5-50 wt % of the total weight of the NP, more preferentially 5-20 wt % total weight of the NP or most preferentially 5-15 wt % of the total weight of the NP. In a particular embodiment, CBZ comprises from 6-13 wt % of the total weight of the NP, more particularly about 6, 7, 8, 9, 10, 11, 12 or 13 wt % of the total weight of the NP.

In one embodiments of the first aspect, the drug delivery system is administrated intraperitoneally. In another embodiment, the drug delivery system comprises pharmaceutically acceptable excipients. In yet another embodiment, the intraperitoneal administration is subsequent to cytoreductive surgery.

In a further embodiment, the cancer is selected from the group consisting of prostate cancer, breast cancer, peritoneal cancer, peritoneal carcinomatosis, glioma, lung cancer, adrenocortical carcinoma, testicular cancer, urothelium transitional cell carcinoma, ovarian cancer and metastasis thereof.

In the embodiment where the cancer is peritoneal carcinomatosis, it may be originated from ovarian cancer, colorectal carcinoma, pancreatic cancer, stomach cancer, hepatocellular carcinoma, gallbladder carcinoma, renal cell carcinoma, transitional cell carcinoma, endometrial, cervical cancers, breast cancer, lung cancer and malignant melanoma.

In a second aspect, a method for treating cancer is provided comprising administering a drug delivery system according to the first aspect to a patient in need thereof.

In a third aspect, a composition or solution comprising the drug delivery system according to the first aspect is provided. The composition or solution may be a pharmaceutical formulation comprising pharmaceutically acceptable excipients and diluents.

DETAILED DESCRIPTION

Definitions

Figure 1:
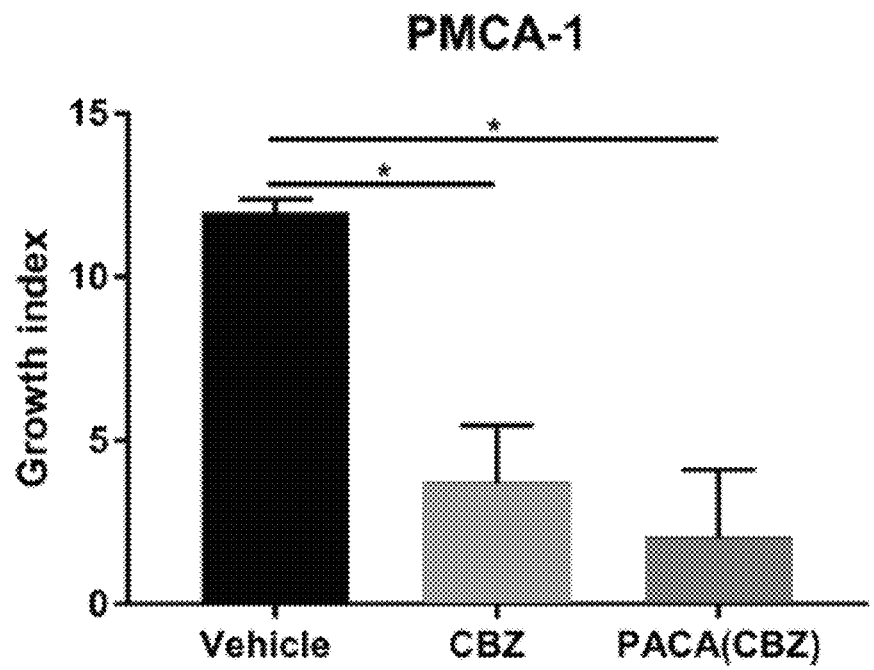
FIG. 1: Growth index in response to treatment with 15 mg/kg CBZ and PACA(CBZ) in PMCA-1. * indicates p<0.05. CBZ: 3/6 mice were cured by the treatment. PACA (CBZ) cured 5/6 mice. The term "cured" refers to the animals that were sacrificed on day 100 with no detectable tumor.

The term 'nanoparticle, (NP)' is used herein to describe particles or capsules with linear dimensions less than 800 nm.

The term "PEGylation" is used herein to describe the process of both covalent and non-covalent attachment or amalgamation of polyethylene glycol (PEG) polymer chains to nanoparticles, which is then described as PEGylated (pegylated). As will be known to the skilled person, the association of PEG to the NP surface can "mask" the NP from the host's immune system by creating a water corona around the NP. This can reduce the immunogenicity and antigenicity of the NP, and prolong its circulatory time by reducing renal clearance. Depending on the density of PEG on the surface, the PEG is classified as being in a brush or mushroom conformation. The PEGylation can be performed either during or after synthesis of the NPs, by either a covalent or noncovalent bond, resulting in varying properties of the PEGylation.

The term "targeting moiety" is used herein to describe any molecule that can be bound to the surface of the NP and result in selective binding to specific cells or biological surfaces.

The term "passive targeting" is used herein to describe the accumulation and/or retention of nanoparticles in inflamed and malignant tissue that occurs due to leaky blood vessels and impaired lymphatic drainage. Passive targeting is independent of targeting moieties on the surface of NPs. The term "enhanced permeability and retention (EPR)" effect is an example of passive targeting and describe the phenomenon where molecules of certain sizes (typically liposomes, nanoparticles, and macromolecular drugs) tend to accumulate in tumor tissue much more than they do in normal tissues upon administration intravenously. The NPs as described herein are typically of a size from about 1-800 nm, such as about 10-500, preferably about 70-150 nm. Accordingly, the EPR effect will allow the NPs as described herein to selectively extravasate and accumulate in tumors.

The term "active targeting" is used herein to describe the accumulation and/or retention of the nanoparticle on specific cells or biological surfaces due to the specific interaction between the targeting moiety and the cell surface or the biological surface.

The terms "intraperitoneal administration" and "administered intraperitoneally" are art recognized terms and include modes of administration via injections intraperitoneally. One type of therapy which is administrated intraperitoneally is intraperitoneal chemotherapy, such as hyperthermic intraperitoneal chemotherapy (HIPEC), where chemotherapy is administrated directly into the peritoneal cavity.

The term "pharmaceutically acceptable" as used herein denotes that the system or composition is suitable for administration to a subject, including a human patient, to achieve the treatments described herein, without unduly deleterious side effects in light of the severity of the disease and necessity of the treatment.

The terms "therapy", "treat," "treating," and "treatment" are used synonymously to refer to any action providing a benefit to a patient at risk for or afflicted with a disease, including improvement in the condition through lessening, inhibition, suppression or elimination of at least one symptom, delay in progression of the disease, prevention, delay in or inhibition of the likelihood of the onset of the disease, etc.

The terms "microbubble associated with nanoparticles" or "nanoparticles associated with microbubbles" are used herein to describe in what way nanoparticles can interact with the microbubble interface. The term "associated with" as used in connection with this include association by any type of chemical bonding, such as covalent bonding, non-covalent bonding, hydrogen bonding, ionic bonding or any other surface-surface interactions.

DESCRIPTION

Described herein is a drug delivery system comprising poly (alkyl cyanoacrylate) (PACA) nanoparticles (NPs) comprising cabazitaxel (CBZ) for treatment of cancer. In a preferred embodiment, the drug delivery system is for intraperitoneal administration.

One embodiment of the invention is a drug delivery system that does not comprise microbubbles (MBs).

The effect of PACA NPs loaded with the cytotoxic drug CBZ is demonstrated in vivo, in two animal models generated by implanting tumor tissue pieces from patients with peritoneal metastases from colorectal cancer or pseudomyxoma peritonei in nude mice.

The peritoneum is a mesothelial lining covering the abdominal cavity (parietal peritoneum) and intraperitoneal organs (visceral peritoneum). This peritoneal lining of the cavity supports many of the abdominal organs and serves as a conduit for their blood vessels, lymphatic vessels, and nerves. The peritoneal cavity contains a small amount of fluid, which circulates under the influence of negative pressure generated by the diaphragm, gravity and bowel peristalsis. This natural flow pattern determines the route of spread of disease processes within the peritoneal cavity. The structures within the intraperitoneal space are called "intraperitoneal" and include the stomach and intestines.

Intraperitoneal injection or IP injection is the injection of a substance into the peritoneum (body cavity). In the past it has more often been applied to animals than to humans. In general, it is preferred when large amounts of blood replacement fluids are needed or when low blood pressure or other problems prevent the use of a suitable blood vessel for intravenous injection.

In animals, it is used predominantly in veterinary medicine and animal testing for the administration of systemic drugs and fluids because of the ease of administration compared with other parenteral methods.

In humans, the method may be used to administer chemotherapy drugs to treat some cancers, for example such as ovarian cancer. Administering chemotherapy directly into the peritoneal cavity permits a several-fold increase in drug concentration to be achieved within the abdominal cavity. According to the invention, intraperitoneal (i.p.) chemotherapy may be used alone or subsequent to cytoreductive surgery.

Cytoreductive surgery is a surgical procedure used to remove tumors affecting the protective lining of the abdomen. When it's paired with hyperthermic intraperitoneal chemotherapy, it considerably increases life expectancy and reduces the rate of cancer recurrence. Hyperthermic intraperitoneal chemotherapy (HIPEC) is a highly concentrated, heated chemotherapy treatment delivered directly to the abdomen during surgery.

While cytoreductive surgery and intraperitoneal (i.p.) chemotherapy may constitute a curative option for some patients, treatment outcome is still highly variable and the search for novel therapies is warranted.

Peritoneal carcinomatosis (PC) is defined as intraperitoneal dissemination of any tumor which is not originated from the peritoneum itself.

PC is most commonly seen in abdominopelvic malignancies. Ovarian cancer is the most common cause (46%) followed by colorectal carcinoma (31%), pancreatic cancer, stomach cancer and other malignancies including the hepatocellular carcinoma, gallbladder carcinoma, renal cell carcinoma, transitional cell carcinoma, endometrial, cervical cancers and unknown primary. Extra-abdominal conditions such as breast cancer, lung cancer and malignant melanoma can involve the peritoneal cavity through the haematogenous spread.

Five human tumors and corresponding orthotopic animal models from human PC derived from colorectal carcinoma or pseudomyxoma peritonei have been extensively characterized by immunohistochemical analysis by the inventors (Flatmark, K., et al., Exploring the peritoneal surface malignancy phenotype—a pilot immunohistochemical study of human pseudomyxoma peritonei and derived animal models. Human Pathology, 2010. 41(8): p. 1109-1119).

As disclosed herein, studies demonstrate effects of NP-encapsulated CBZ in two of these models, namely the ones denoted PMCA1 and PMCA3. It is demonstrated that NP-encapsulated CBZ has similar or even better efficacy than similar concentrations of non-encapsulated drug. Few drugs are active in the treatment of peritoneal metastases from colorectal cancer and pseudomyxoma peritonei. In principle, several of the drugs used in standard-of-care treatment of metastatic colorectal cancer are relevant in this setting, however, none of these drugs are considered very efficacious in the treatment of peritoneal disease. For patients with pseudomyxoma peritonei in particular, no systemic chemotherapy is considered efficacious. Accordingly, this particular group of patients has a high unmet need for treatment. In summary, encapsulation of CBZ in PACA NPs is a promising alternative to the clinically available formulation of the drug.

Studies has been conducted to demonstrate effects of PACA NPs loaded with the cytotoxic drug CBZ in in vivo models with peritoneal carcinomatosis (PC) by intraperitoneal administration. Primary cancer occurring in the abdominal organs (e.g. ovary, colon and rectum, stomach and pancreas) often leads to the migration of cancer cells to the peritoneal cavity resulting in the formation of peritoneal carcinomatosis. As an alternative route of administration, intraperitoneal (IP) chemotherapy were tested in two different mouse models, both demonstrating an improved efficacy of PACA NPs loaded with CBZ compared to IP therapy with CBZ alone. The intraperitoneal administration was performed with intraperitoneal injections.

Without being bound by theory, it is hypothesized that the improved results achieved with IP therapy is due to the high local drug concentration achieved with PACA NPs loaded with the cytotoxic drug CBZ in the peritoneum. By encapsulating the drug, an enhanced retention of the drug is achieved compared to administration of free drug. In addition, there may be an interaction between tumors in the peritoneum and the PACA NPs, further enabling a high concentration of drugs reaching the tumors. An additional benefit of the intraperitoneal administration is that systemic toxicity is reduced compared to parental injections into the blood, in particular when the drug is encapsulated.

As will be understood by a person skilled in the art, the invention as disclosed herein is different in form compared to the drug delivery system as described in Snipstad et al. (*Ultrasound Med Biol* 2017, 43 (11), 2651-2669). As described herein, the drug delivery system of the invention is not administrated intravenously, and it does not comprise NP-stabilized MBs, as is described by Snipstad et al. (2017). In different embodiments, the drug delivery system according to the invention does not comprise NPs that stabilize the MBs nor NPs that are used to stabilize gas-filled MBs. Accordingly, the drug delivery system described herein is not dependent on ultrasound to achieve treatments effects, in contrast to the delivery system described in Snipstad et al. (Ultrasound Med Biol 2017, 43 (11), 2651-2669), which is ultrasound-mediated. Accordingly, in one embodiment as disclosed, the drug delivery system is not mediated by an acoustic field, such as ultrasound or focused ultrasound.

In a further embodiment, the drug delivery system does not comprise NPs that are associated with the MB. It is also disclosed a drug delivery system that does not comprise gas-filled MBs. In yet a further embodiment, the drug delivery system does not comprise MBs.

A preferred embodiment as provided herein is a drug delivery system comprising PEGylated PACA NPs loaded with CBZ, or a pharmaceutically acceptable salt thereof, for treatment of cancer, by administration in the peritoneal cavity to a subject in need thereof. Compared with intravenous (IV) treatment, intraperitoneal (IP) administration permits a several-fold increase in drug concentration to be achieved within the abdominal cavity. Accordingly, the drug delivery system of the invention is for administration intraperitoneally.

In one embodiment, the drug delivery system of the invention is for treatment of cancer by intraperitoneal chemotherapy, such as hyperthermic intraperitoneal chemotherapy.

In one embodiment, the administration is performed using intraperitoneal injections.

In another embodiment, the intraperitoneal administration of the drug delivery system is subsequent to cytoreductive surgery.

Degradation rate of PACA NPs can be controlled by the choice of the alkyl chain of the cyanoacrylate monomer, as demonstrated by Sulheim et al. (Sulheim et al. Cellular uptake and intracellular degradation of poly(alkyl cyanoacrylate) nanoparticles. J Nanobiotechnology. 2016 Jan. 8; 14:1). It has also been demonstrated, using a panel of cell lines, that the cytotoxicity is dependent on the monomers used, i.e. n-butyl-, 2-ethyl-butyl-, or octyl cyanoacrylate (BCA, EBCA and OCA, respectively), see Sulheim et al (Sulheim et al. *Cytotoxicity of Poly(Alkyl Cyanoacrylate) Nanoparticles*. Int J Mol Sci. 2017 Nov. 18; 18(11)).

In different embodiments of the invention, the alkyl chain of the cyanoacrylate monomer is a linear or branched C4-C10 alkyl chain. In preferred embodiments the monomer used is selected from the group consisting of n-butyl-(BCA), 2-ethyl butyl (EBCA), polyisohexyl (IHCA) and octyl cyanoacrylate (OCA). Accordingly, in different embodiments, the drug delivery system comprises NPs selected from the group consisting of PBCA (Poly (butyl cyanoacrylate)), PEBCA (poly (ethylbutylcyanoacrylate)), PIHCA (poly (isohexylcyanoacrylate)) and POCA (poly (octyl cyanoacrylate)).

As described herein, the NPs are PEGylated, i.e. coated with a hydrophilic polymer such as polyethylene glycol (PEG).

In different embodiments of the invention, the NPs are PEGylated with PEG-comprising molecules selected from the group consisting of Je□amine® (polyetheramines), Brij® (polyoxyethylene stearyl ether), Kolliphor® (polyethoxylated castor oil), Pluronic® (ethylene oxide-propylene oxide block copolymers) or combinations thereof.

According to an embodiment, the NPs are PEGylated with the PEG-comprising molecules selected from Pluronic® and Kolliphor®.

According to another embodiment, the NPs are PEGylated with the PEG-comprising molecules selected from Brij® and Kolliphor®.

In an embodiment of the invention, the PACA NPs is produced by a miniemulsion anionic polymerization process, in particular a one-step process as described in WO2014/191502, both with or without targeting moieties.

By using NPs that is further surface modified with targeting moieties, for example by using NPs prepared by miniemulsion anionic polymerization technique with polyalkylene glycols that is covalently attached to a targeting moiety, one can enable active targeting and potentially enhanced retention at specific locations, such as in tumors or diseased tissue. Also, this can facilitate uptake in cancer cells that is dependent upon specific ligand-receptor interactions.

The targeting moiety may be any suitable moiety that causes the NPs to bind specifically at targeted locations.

Preferably, the targeting moiety has a molecular weight in the range of 100 to 200000 Da, more preferably 200 to 50000 Da, even more preferably 300 to 15000 Da.

It should be appreciated that a single targeting moiety or a mixture of different targeting moieties may be used.

Example targeting moieties are selected from the group consisting of an amino acid, protein, peptide, antibody, antibody fragment, saccharide, carbohydrate, glycan, cytokine, chemokine, nucleotide, lectin, lipid, receptor, steroid, neurotransmitter, cell surface marker, cancer antigen, glycoprotein antigen, aptamer or mixtures thereof. Particularly preferred targeting moieties include linear and cyclic peptides. In one embodiment, the targeting moiety does not belong to the group consisting of amino acids and lipids.

It is previously known that the size of nanoparticles influences the targeting effects of the nanoparticles when they are administrated systemically into the blood, as they accumulate in the areas around tumors with leaky vasculature. This is known as 'enhanced permeability and retention' (EPR) effect in tumor tissue. The EPR effect is as a type of targeting, commonly referred to as "passive targeting". Traditionally, tumor targeting approaches are classified into 'passive targeting' and 'active targeting'. The EPR effect will be known to the skilled person as a form of passive targeting. The introduction of targeting moieties on the surface of the NP will be known to the skilled person as a type of active targeting.

The NPs used in the examples contain the cytotoxic drug cabazitaxel (CBZ). CBZ is a semi-synthetic taxane derivative that inhibits microtubule disassembly. CBZ has a very low water solubility, which complicates the administration of the free, non-encapsulated drug.

However, as demonstrated in the examples, due to excellent compatibility and solubility of CBZ in alkyl cyanoacrylate monomers, high concentrations of the drug can be dissolved in alkyl cyanoacrylate monomer solution and thus become encapsulated in PACAs.

According to different embodiments, the loading capacity of CBZ in NPs can be 1-90 wt % of the total weight of the NP, preferentially 5-50 wt % of the total weight of the NP. In particularly preferred embodiments, the loading capacity of CBZ is from 5-15 wt % of the total weight of the NP, such as 5, 6, 7, 8, 9, 10, 11, 12, 13, 14, 15 wt % of the total weight of the NP.

Accordingly, the drug delivery system described herein has a high loading capacity, which is shown to influence the treatment effects of the composition.

As CBZ is insoluble in water, the conventional formulation is CBZ solubilized in a polysorbate 80 solution. As used herein, non-encapsulated or free CBZ refers to the conventional formulation.

CBZ has been included in several clinical trials that study the effects on different types of cancer including several types of prostate cancer, adrenocortical carcinoma, testicular cancer, urothelium transitional cell carcinoma and ovarian cancer.

In the clinical studies, it has been demonstrated that the efficacy of CBZ is accompanied by serious side effects and deaths due to toxicity. The toxicity rates observed in clinical trials have been assumed to pose an obstacle to use and management of CBZ, a drug that, on the other hand, has demonstrated great activity. In the transition from clinical trial to clinical practice, it has been speculated that CBZ will not be used much because of the risk of side effects, as well as high cost and discomfort derived from the administration regimes and the lack of patient compliance with the administration regimes previously proposed for CBZ-treatments. Thus, limiting the administration regimes, for example from tree-weekly to weekly has been proposed in treatment of for example prostate cancer, to improve hematologic tolerance along with a better therapeutic range to be able to increase the dose intensity and activity without increasing the associated toxicity.

Accordingly, the advantage that drug-loaded NPs give less adverse effects than free drug makes the drug delivery system as described by the inventors highly relevant for CBZ. Encapsulating CBZ in NPs offers a more sustained release profile of the drug, which can ameliorate parts of the toxicity and allows for administration of higher doses. The reduction of adverse effects allows for administration of increased doses of drugs. Accordingly, encapsulation of drug in the NPs will further improve the treatment effects. Accordingly, the inventors propose the idea that the drug delivery system as described herein will enhance treatments effects and/or reduce side effects when used in treatment of cancer.

In different embodiments, the invention provides a drug delivery system comprising optionally PEGylated PACA NPs loaded with CBZ, or a pharmaceutically acceptable salt thereof, for treatment of cancer, wherein the cancer is selected from the group consisting of prostate cancer, breast cancer, peritoneal cancer, such as peritoneal carcinomatosis, glioma, lung cancer, adrenocortical carcinoma, testicular cancer, urothelium transitional cell carcinoma and ovarian cancer. In different embodiments, the peritoneal carcinomatosis can originate from ovarian cancer, colorectal carcinoma, pseudomyxoma peritonei, pancreatic cancer, stomach cancer and other malignancies including the hepatocellular carcinoma, gallbladder carcinoma, renal cell carcinoma, transitional cell carcinoma, endometrial, cervical cancers, breast cancer, lung cancer and malignant melanoma. In two particular embodiments, the cancer is a peritoneal carcinomatosis originating from colorectal cancer or pseudomyxoma peritonei.

According to an embodiment, the drug delivery system is provided in a composition to be administered intraperitoneally. The compositions can optionally comprise pharmaceutically acceptable carriers and excipients.

An aspect of the invention includes a method of treating cancer comprising administering a drug delivery system according to the first to a subject in need thereof. Exemplary subjects include mammalian subjects such as human subjects.

EXAMPLES

Example 1

Materials and Methods

Synthesis and Characterization of Nanoparticles.

PEGylated PEBCA NPs were synthesized by miniemulsion polymerization. An oil phase consisting of 2.5 g 2-ethylbutyl cyanoacrylate (monomer, Cuantum Medical Cosmetics, Spain) containing 0.2% (w/w) butylated hydroxytoluene (Fluka, Switzerland) and 2% (w/w) Miglyol® 812 (Cremer, USA) was prepared. Particles containing cytostatic drug for treatment were prepared by adding CBZ (10% (w/w), Biochempartner Co. Ltd., China, product item number BCP02404) to the oil phase.

An aqueous phase consisting of 0.1M HCl (20 ml) containing Brij®L23 (6 mM, Sigma, USA) and Kolliphor® HS15 (6 mM, Sigma, Germany) was added to the oil phase and immediately sonicated for 3 min on ice (6×30 sec intervals, 60% amplitude, Branson Ultrasonics digital sonifier 450, USA). The solution was rotated (15 rpm, SB3 rotator, Stuart, UK) at room temperature overnight before adjusting the pH to 5 using 1M NaOH. The polymerization was continued for 5 h at room temperature on rotation. The dispersion was dialyzed (Spectra/Por® dialysis membrane MWCO 100,000 Da, Spectrum Labs, USA) against 1 mM HCl to remove unreacted PEG. The size, polydispersity index (PDI) and the zeta potential of the NPs were measured by dynamic light scattering and laser Doppler Micro-electrophoresis using a Zetasizer Nano ZS (Malvern Instruments, UK). To calculate the amount of encapsulated drug, the drug was extracted from the particles by dissolving them in acetone (1:10), and quantified by liquid chromatography coupled to mass spectrometry (LC-MS/MS) as described below.

CBZ quantification by LC-MS/MS. CBZ, as the pure chemical or part of NPs, was quantified by LC-MS/MS, using an Agilent 1290 HPLC system coupled to an Agilent 6490 triple quadrupole mass spectrometer. The HPLC column was an Ascentis® Express C8, 75×2.1 mm, 2.7 μm particles size with a 5×2.1 mm guard column of the same material (Sigma), run at 40° C. Eluent A was 25 mM formic acid in water and eluent B was 100% methanol, and flow rate was 0.5 ml/min. The mobile phase gradient was isocratic at 55% B for 1.5 min, then from 55% to 80% B over 1 min, followed by 1 min washout time and subsequently column re-equilibration. Injection volume was 5.00 μl. MS detection was in positive ESI mode (Agilent Jetstream) quantified in multiple reaction monitoring (MRM) mode using the transition m/z 858.3→577.2. The parent ion was chosen to be the Na adduct as this gave the best sensitivity. Similarly, the hexadeuterated internal standard was detected on the 864.4→583.2 transition. Both analytes were run at 380 V fragmentor and 20 V collision energy.

Reference standards were used for accurate quantification. The unlabeled CBZ standard was the same as used for synthesis (see above) at >98% purity. Hexadeuterated CBZ internal standard was purchased from Toronto Research Chemicals (Toronto, Canada; catalogue number C046502 at 99.6% isotopic purity). Standards were dissolved in acetone and were used to build an unlabeled standard series spanning at least five concentration points.

The limit of quantification (LOQ) was calculated from six replicate quantifications of the lowest concentration point in the standard curves (0.1 ng/ml), specifically as the average plus six standard deviations; this amounted to an LOQ of 0.19 ng/ml (signal/noise ratio>20). Accuracy based on the same standard sample set was 8.8% and precision was 18.0%.

Example 2

In Vivo Treatments Effects in Two Animal Models
Methods

The models were generated by implanting tumor tissue pieces from patients with peritoneal metastases from colorectal cancer or pseudomyxoma peritonei in nude mice (Flatmark, K., et al., *Pseudomyxoma peritonei—two novel orthotopic mouse models portray the PMCA-I histopathologic subtype*. BMC Cancer, 2007. 7: p. 116; Flatmark, K., et al., *Exploring the peritoneal surface malignancy phenotype—a pilot immunohistochemical study of human pseudomyxoma peritonei and derived animal models*. Human Pathology, 2010. 41(8): p. 1109-1119; Flatmark, K., et al., *Immunotoxin targeting EpCAM effectively inhibits peritoneal tumor growth in experimental models of mucinous peritoneal surface malignancies*. Int J Cancer, 2013. 133(6): p. 1497-506). Passage to new generations of mice is performed by injection of mucinous tumor tissue into the peritoneal cavity. For initiation of experiments, 200 µl mucinous tumor from donor mice was injected intraperitoneally. Treatment was initiated the following day to simulate the clinical situation after cytoreductive surgery where all visible tumor has been removed.

Cabazitaxel (CBZ) in Polysorbate 80 was diluted in 13% ethanol, and further diluted in 0.9% NaCl to a concentration of 0.60 or 0.75 mg/ml. PACA(CBZ) was synthesized as described in Example 1, and further dissolved in 0.9% NaCl. A dose of 15 mg/kg was injected intraperitoneally in a volume of 20 or 25 µl/g (mouse body weight) to groups of 5-6 mice. The control group received injections of vehicle consisting of 13% ethanol in 0.9% NaCl to mimic the CBZ solvent. The animals were sacrificed when abdominal distention caused by tumor growth was clearly visible as assessed by an experienced animal technician. To compare tumor growth in different treatment groups a growth index was calculated by combining the two key parameters survival (time in days) and tumor growth (weight in g) using the equation:

$$\text{Growth index} = \text{tumor weight} + ((T_{total} - T_A)/T_{Total}) \times 10$$

$T_A$ is the survival time for each animal, and $T_{Total}$ is the total duration of the experiment (in this case 0.100 days).

RESULTS

Two experiments were performed in models PMCA1 (derived from patient with colorectal cancer) and PMCA3 (derived from patient with pseudomyxoma peritonei) and demonstrated an increased treatments effects of PACA (CBZ) compared to negative control (Vehicle, consisting of 13% ethanol in 0.9% NaCl) and CBZ (in Polysorbate 80, diluted in 13% ethanol, and further diluted in 0.9% NaCl to a concentration of 0.60 or 0.75 mg/ml).

The results in the PMCA1 model is shown in FIG. 1 and demonstrates growth index in response to treatment with 15 mg/kg CBZ and PACA(CBZ) in PMCA-1.

All vehicle-treated animals were sacrificed because of tumor growth. CBZ significantly inhibited tumor growth compared to vehicle treatments and ⅜ mice were cured by the treatment (i.e. sacrificed on day 100 with no detectable tumor). PACA(CBZ) cured ⅝ mice and significantly inhibited tumor growth compared to vehicle treatment. Even though the difference between the CBZ and PACA(CBZ) groups was not statistically significant, it was a clear tendency toward an increased treatment effect in the group where mice where given PACA (CBZ). Since this model was very sensitive to CBZ, lower doses of CBZ could be tested to further explore a potential advantage of incapsulating the drug.

Without being bound by theory, it is hypothesized that the PACA particles interact with the tumors in some ways, enabling an increased uptake of the encapsulated drug. This could explain the tendency towards the increased effects.

Figure 2:
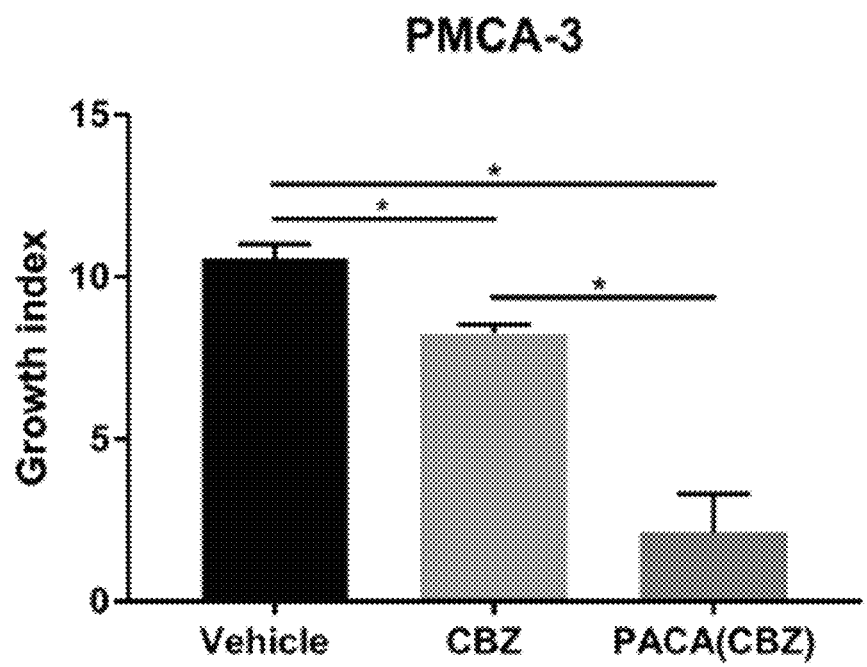
FIG. 2. Growth index in response to treatment with 15 mg/kg CBZ and PACA(CBZ) in PMCA-3. * indicates p<0.05. All vehicle-treated animals were sacrificed because of tumor growth. No animals were cured in the CBZ group. In the group treated with PACA(CBZ), 2/5 mice were cured.

The results in the PMCA3 model is shown in FIG. 2 and demonstrate the growth index in response to treatment with 15 mg/kg CBZ and PACA(CBZ) in PMCA-3.

All vehicle-treated animals were sacrificed because of tumor growth. CBZ alone significantly reduced tumor growth in this model compared to vehicle treatment, but no animals were cured. PACA(CBZ) treatment significantly inhibited tumor growth compared to vehicle treatment and CBZ alone, and ⅖ mice were cured.

The invention claimed is:

1. A method for treatment of cancer in a subject, the method comprising intraperitoneally injecting the subject with a poly (alkyl cyanoacrylate) nanoparticle, the nanoparticle comprising 6 to 20 wt % cabazitaxel based on the total weight of the nanoparticle and having a size of 10 to 500 nanometers, wherein the nanoparticle does not include a targeting moiety, wherein the cabazitaxel is encapsulated by the nanoparticle, and wherein the nanoparticle is administered to the subject in an amount sufficient to treat the cancer in the subject,
    wherein the cancer is peritoneal carcinomatosis originating from ovarian cancer, colorectal carcinoma, cervical cancer, breast cancer, colon cancer, or prostate cancer, or is pseudomyxoma peritonei, and
    wherein the poly(alkyl cyanoacrylate) comprises a cyanoacrylate having a 2-ethyl butyl (EBCA) alkyl chain.

2. The method of claim 1, wherein the nanoparticle is administered in an amount sufficient to inhibit the metastasis of the cancer in the subject and the method comprises inhibiting metastasis in the subject.

3. The method of claim 1, wherein the nanoparticle is produced according to a miniemulsion anionic polymerization process.

4. The method of claim 3, wherein the nanoparticle has a particle size of 70 to 150 nanometers.

5. The method of claim 3, wherein the nanoparticle is PEGylated.

6. The method of claim 1, wherein intraperitoneally injecting is subsequent to cytoreductive surgery.

7. The method of claim 1, wherein the cancer is peritoneal carcinomatosis originating from ovarian cancer or colorectal carcinoma, or is pseudomyxoma peritonei.

* * * * *